(12) United States Patent
Nanjo et al.

(10) Patent No.: US 12,151,123 B2
(45) Date of Patent: Nov. 26, 2024

(54) PHOTOTHERAPY DEVICE

(71) Applicant: Teijin Pharma Limited, Tokyo (JP)

(72) Inventors: Takuya Nanjo, Tokyo (JP); Naoya Ishibashi, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 363 days.

(21) Appl. No.: 17/635,571

(22) PCT Filed: Dec. 22, 2020

(86) PCT No.: PCT/JP2020/048017
§ 371 (c)(1),
(2) Date: Feb. 15, 2022

(87) PCT Pub. No.: WO2021/132271
PCT Pub. Date: Jul. 1, 2021

(65) Prior Publication Data
US 2022/0266053 A1 Aug. 25, 2022

(30) Foreign Application Priority Data

Dec. 23, 2019 (JP) .................................. 2019-231711

(51) Int. Cl.
*A61N 5/067* (2006.01)
*A61N 5/06* (2006.01)

(52) U.S. Cl.
CPC ...... *A61N 5/067* (2021.08); *A61N 2005/0664* (2013.01)

(58) Field of Classification Search
CPC ............ A61N 5/067; A61N 2005/0664; A61N 2018/00011; A61N 5/0616; A61N 2005/007; A61B 2018/00035; A61B 2018/00452; A61B 18/203; A61B 90/04; A61B 2090/049; A61B 2018/00005; A61B 2018/00476
See application file for complete search history.

(56) References Cited

U.S. PATENT DOCUMENTS

| 5,344,418 A | 9/1994 | Ghaffari |
| 6,638,272 B2 | 10/2003 | Cho et al. |

(Continued)

FOREIGN PATENT DOCUMENTS

| JP | 2002-272861 A | 9/2002 |
| JP | 2011-515201 A | 5/2011 |
| WO | 2009/120876 A2 | 10/2009 |

OTHER PUBLICATIONS

International Search Report for PCT/JP2020/048017, dated Feb. 16, 2021 (PCT/ISA/210).

*Primary Examiner* — Yingchuan Zhang
*Assistant Examiner* — Sebastian X Lukjan
(74) *Attorney, Agent, or Firm* — Sughrue Mion, PLLC (57) ABSTRACT

A phototherapy device includes a laser light source 8 for emitting laser light toward a target portion, a body part 5, an intake port 12 provided at a side surface of the body part 5, a discharge port 13 provided at the side surface of the body part 5 at an opposite side from the intake port 12, and an air supply device 14 for supplying air to be ejected from the intake port 12 to the inside of the body part 5, the intake port 12 configured so that an ejection direction F0 of the air is toward the near side from a center of an emission area A of the laser light at the target portion T.

6 Claims, 7 Drawing Sheets

(56) References Cited

U.S. PATENT DOCUMENTS

| | | |
|---|---|---|
| 2002/0183724 A1 | 12/2002 | Neev |
| 2003/0181893 A1 | 9/2003 | Neuberger |
| 2010/0121418 A1 | 5/2010 | Lee et al. |
| 2012/0197357 A1* | 8/2012 | Dewey ................ A61N 5/0616 607/89 |
| 2019/0015681 A1 | 1/2019 | Pyun et al. |
| 2019/0274608 A1 | 9/2019 | Choi |

* cited by examiner

PHOTOTHERAPY DEVICE

CROSS REFERENCE TO RELATED APPLICATIONS

This application is a National Stage of International Application No. PCT/JP2020/048017, filed Dec. 22, 2020, claiming priority based on Japanese Patent Application No. 2019-231711, dated Dec. 23, 2019.

FIELD

The present invention relates to a phototherapy device.

BACKGROUND

Phototherapy devices can be used to emit laser light toward living tissue for the purpose of promoting blood circulation, promoting the metabolism, and other therapy or assisted therapy. In particular, in the laser classes in the JIS C 6802 safety standards for lasers, if using a class 3 or higher high output phototherapy device for home therapy, compliance with class 1C becomes an essential requirement.

In this regard, if the portion or condition of a predetermined location of the skin of the target tissue or the extents of the color of the skin, moles, and body hair differ, even when emitting laser light by the same output for the same time, the amount of heat energy which is absorbed by the skin will differ. In particular, in races with entirely black skin or people with thick black body hair, the absolute amount of heat energy which is absorbed becomes greater and there is a possibility of being burned.

To prevent burns due to emission of laser light, there is known a phototherapy device provided with a cooling device for cooling a target portion of laser light utilizing a cooling fluid, for example, cooling air (PTL 1). The cooling device described in PTL 1 ejects cooling air through a pipe.

CITATION LIST

Patent Literature

PTL 1: Japanese Unexamined Patent Publication No. 2002-272861

SUMMARY

Technical Problem

PTL 1 only describes ejecting cooling air over an area somewhat broader than the area of the convergent light, and does not describe anything about the optimum direction of ejection, i.e., the angle of the pipe, etc. Further, PTL 1 does not describe how the pipe is attached to a handpiece. The effect received due to the cooling air ejected also differs, in accordance with whether this is at the inside or the outside of the handpiece. As a result, in the cooling device described in PTL 1, it is questionable as to whether the target portion is efficiently cooled.

The present invention has as its object to provide a phototherapy device provided with a cooling device able to efficiently cool a target portion.

Solution to Problem

According to one aspect of the present invention, there is provided a phototherapy device comprising a laser light source for emitting laser light toward a target portion, a body part, an intake port provided at a side surface of the body part, a discharge port provided at the side surface of the body part at an opposite side from the intake port, and an air supply device for supplying air to be ejected from the intake port to the inside of the body part, the intake port configured so that an ejection direction of the air is toward the near side from a center of an emission area of the laser light at the target portion.

The discharge port may be provided at the side surface of the body pan near a front end part, and the intake port may be provided at a position further away from the front end part of the body part than the discharge port. The air supply device may have a fan arranged adjoining the side surface of the body part and a duct connecting the fan and the intake port and be configured so that the fan generates an air flow in a direction away from the side surface of the body part. The phototherapy device may further comprise an optical sensor having a light emitting part for emitting light toward the target portion and a light receiving part for receiving light reflected from the target portion and detecting an approach of the laser light source to the target portion up to a predetermined distance, the light emitting pan and the light receiving part of the optical sensor being arranged inside the body part so as to be exposed to air ejected from the intake port. The optical sensor may be arranged away from a flow path directly from the intake port to the discharge port.

Advantageous Effects of Invention

According to this aspect of the present invention, the common effect is exhibited of provision of a phototherapy device provided with a cooling device able to efficiently cool a target portion.

DESCRIPTION OF EMBODIMENTS

Below, while referring to the drawings, an embodiment of the present invention will be explained in detail. Throughout the drawings, corresponding component elements will be assigned common reference notations.

Figure 1:
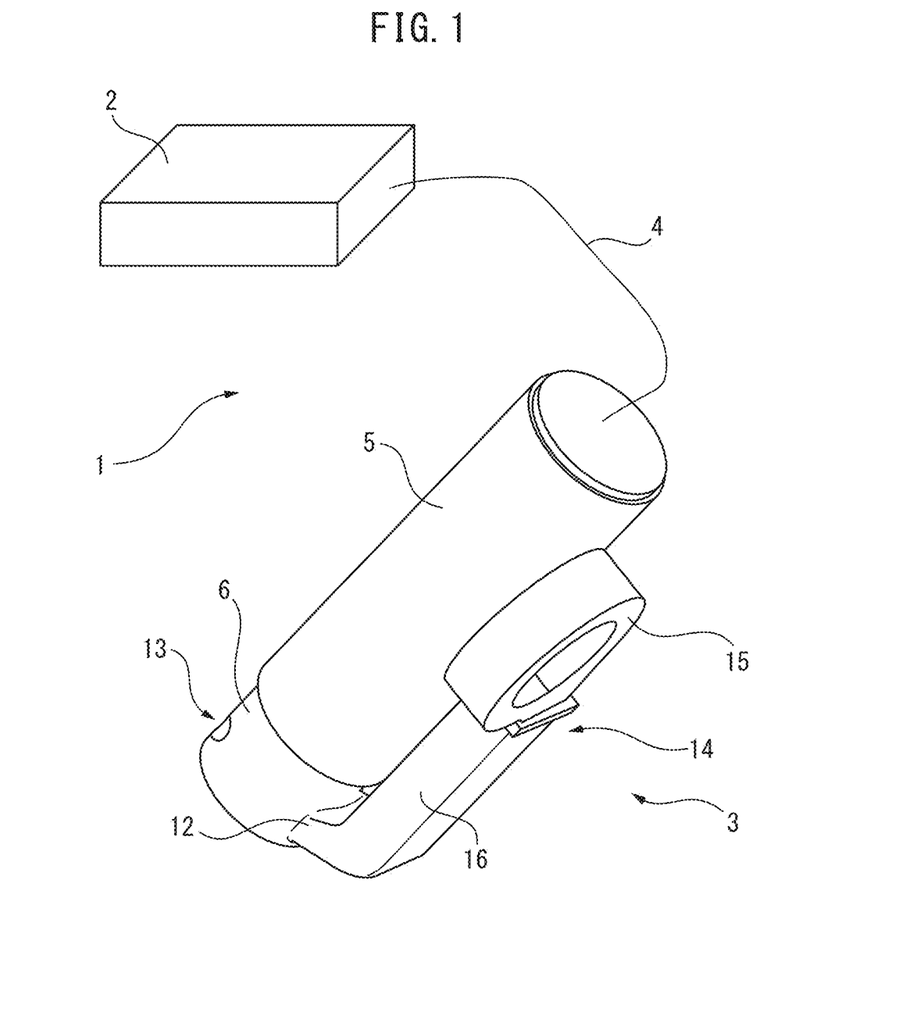
FIG. 1 is a schematic view of a phototherapy device according to an embodiment of the present invention.

FIG. 1 is a schematic view of a phototherapy device 1 according to an embodiment of the present invention, while FIG. 2 is a view showing an operation of a probe 3.

The phototherapy device 1 has a control device 2, probe 3, and cable 4 electrically connecting the control device 2 and probe 3. The control device 2 has one or more processors, a storage part and its peripheral circuits, etc. The control device 2 comprehensively controls the overall operation of the probe 3 based on a computer program stored in advance in the storage part. At the time of this processing, the control device 2 receives signals of various sensors such as the later explained optical sensors, etc. and sends control signals relating to emission and stopping of the laser light and startup and stopping of a fan, etc. The control device 2 may also have an input/output part, for example, a display or other display part, and operating buttons or a touch screen or other input interface.

The probe 3 has a cylindrical body part 5. The body part 5 has a cylindrical moving part 6 arranged inside the body pan 5 to be able to move along an axial direction of the body part 5, four optical sensors 7, a laser light source 8 arranged at an inside of the body part 5, an optical window 9 provided at a front surface of the body part 5, and a limit switch 10 arranged inside the body part 5. The moving part 6 is biased by a not shown elastic member to the front with respect to the body part 5. The moving part 6 may also be formed integrally with the body part 5. The laser light emitted from the laser light source 8 passes through the optical window 9 and is emitted to the target portion T through the opening 11 provided at the front end face of the moving part 6. The part of the surface of the target portion T which the laser light is emitted to will be referred to as the "emission area A" of the laser light (FIG. 2(B)).

At the side surface of the body part 5, specifically the side surface of the moving part 6, an intake port 12 is provided. At the side surface of the body part 5 at the opposite side to the intake port 12, specifically the side surface of the moving part 6, a discharge port 13 is provided. The discharge port 13 is provided at the body part 5 near the front end part, specifically the side surface of the moving part 6 near the front end part, while the intake port 12 is provided at a position further away from the front end part than the discharge port 13.

The probe 3 has an air supply device 14 for supplying the air to be ejected from the intake port 12 to the inside of the body part 5. The air supply device 14 has a fan 15 arranged adjoining a side surface of the body part 5 and a duct 16 connecting the fan 15 and the intake port 12. Therefore, air taken in due to rotation of the fan 15 is guided through the duct 16 to the intake port 12. Note that the duct 16 is configured to be able to stretch in accordance with movement of the moving part 6 inside the body part 5 along an axial direction, i.e., movement of the intake port 12.

The fan 15 is configured so as to generate an air flow in a direction away from the side surface of the body part 5. In other words, the shape of the blades of the fan 15 and the direction of rotation of the fan 15 are determined so that such an air flow is generated. Due to the air flow in a direction away from the side surface of the body part 5, heat is removed from the surface of the body part 5, so the body part 5 and in turn the probe 3 as a whole can be cooled.

The optical sensors 7 and the limit switch 10 are arranged inside of the probe 3. The four optical sensors 7 are arranged so as not to contact the surface of the target portion at the time of use. Further, the optical sensors 7 and the limit switch 10 are arranged so as not to obstruct movement of the moving part 6 and emission of laser light by the laser light source 8.

The four optical sensors 7 are arranged inside the body part 5, specifically inside the front end part of the moving part 6, at equal intervals along the circumferential direction. The optical sensors 7 are all arranged away from the flow path of the air directly heading from the intake port 12 to the discharge port 13. In other words, none of the optical sensors 7 is arranged on the virtual flow path directly connecting the intake port 12 and the discharge port 13. Due to this, the optical sensors 7 present little obstruction to the air flow F.

The phototherapy device 1 may also be made to have one, two, or three optical sensors 7 or have five or more optical sensors 7. If the phototherapy device 1 has a plurality of optical sensors 7, the plurality of optical sensors 7 are preferably arranged at equal intervals along the circumferential direction.

Each of the one or more optical sensors 7 configures a detection part. Overall, they configure a distance detection part for detecting a distance up to the target portion T and outputting distance signals corresponding to the distance. The output distance signals are detected by the control device 2. Each optical sensor 7 has a not shown light emitting part for emitting light toward the target portion T and a not shown light receiving part for receiving light reflected from the target portion T. The optical sensor 7 evaluates the distance to the target portion T by the change of the intensity of the reflected light received by the light receiving part. Using the distance signals, it is possible to for example calculate the distance from the laser light source 8 to the target portion T. The distance detection part may be comprised of other sensors etc. as well, so long as they are able to detect the distance to the target portion T and output distance signals corresponding to the distance.

Note that, as explained above, the optical sensors 7 are arranged away from the flow path of the air directly heading from the intake port 12 to the discharge port 13, but the light emitting parts and the light receiving parts of the optical sensors 7 are arranged so as to be exposed to the air ejected from the intake port 12. As a result, it is possible to remove dust or dirt deposited on the surfaces of the light emitting parts and the light receiving parts of the optical sensors 7 by the air flow and ensure the optical sensors 7 constantly function normally.

In the laser classes in the JIS C 6802 safety standards for lasers, when using a phototherapy device 1 mounting a class 3 or higher high output laser light source 8 for home therapy, the phototherapy device 1 must comply with class 1C, but the invention is not limited to this, i.e. it is possible to use a laser light source 8 complying with home therapy by other standards as well.

Figure 2A:
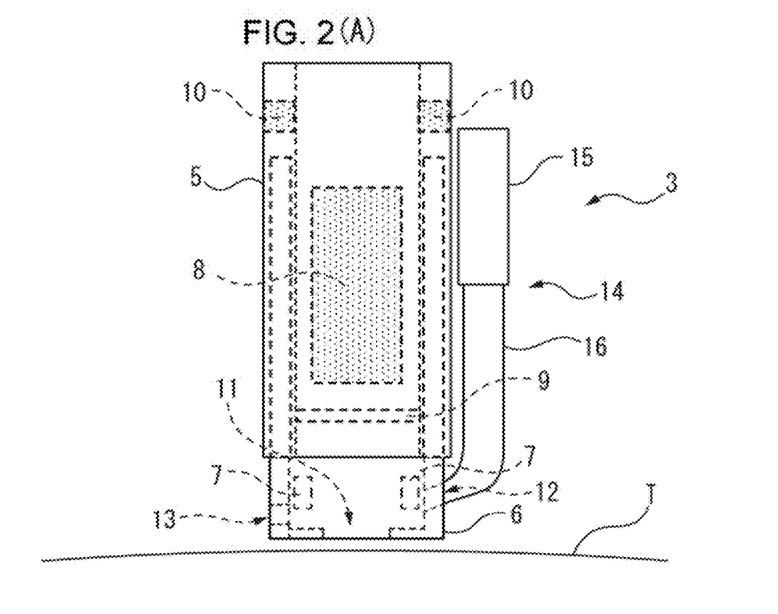
FIG. 2 is a view showing an operation of a probe.
Figure 2B:
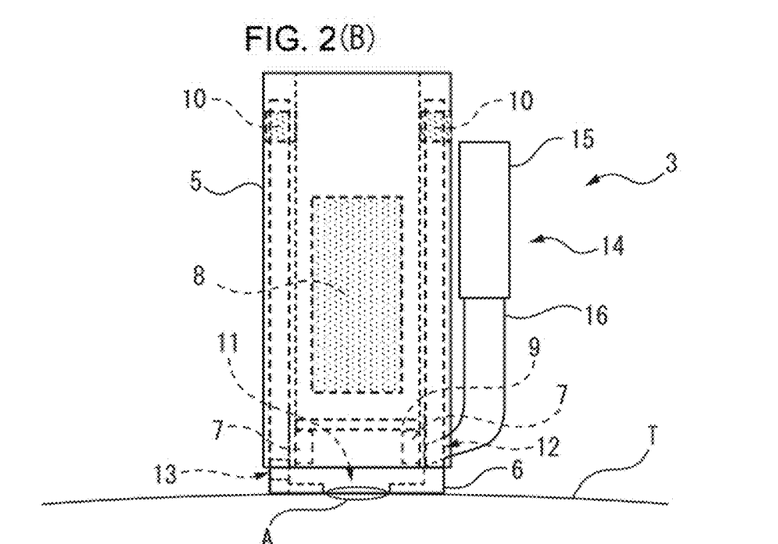

FIG. 2(A) shows the state before pressing the probe 3 against the living target tissue, that is, the target portion T, while FIG. 2(B) shows the state of pressing the probe 3 against the target portion T. Therefore, the front end part of the body part 5, that is, the moving part 6, abuts against the living target tissue, that is, the target portion T. By pressing the probe 3 against the target portion T from the state shown in FIG. 2(A), the moving part 6 retracts and the limit switch 10 turns ON (FIG. 2(B)). In other words, the limit switch 10 configures a proximity detection part for detecting the approach of the laser light source 8 to the target portion T up to a predetermined distance to output a proximity signal. The proximity signal which is output is detected by the control device 2. On the other hand, when the pressing action of the probe 3 against the target portion T is released, the moving part 6 retracts by the biasing force of an elastic member and the limit switch 10 turns OFF (FIG. 2(A)).

In the phototherapy device 1, if a proximity signal output by the limit switch 10 turning ON is detected, emission of laser light by the laser light source 8 to the target portion T is permitted by the control device 2 and laser light is emitted. At this time, it is also possible to not emit laser light if distance signals showing the approach to a predetermined distance are not detected from all of the four optical sensors 7. Further, the fan may be made to start up and stop in accordance with the emission and stopping of laser light. Due to this, it is possible to cool the target portion T only when laser light has been emitted, thus preventing unnecessary cooling of the target portion T.

Below, referring to FIG. 3 to FIG. 7, the result of preparation of a model and fluid analysis based on an embodiment of the present invention will be explained.

Figure 3:
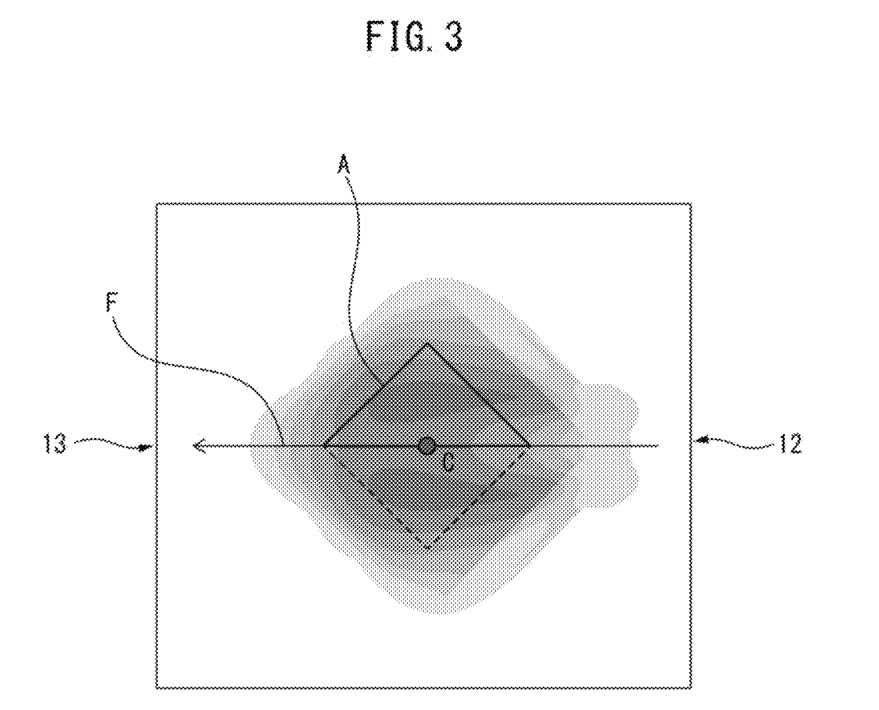
FIG. 3 is a view of an emission area of laser light at a target portion seen from directly above.

FIG. 3 is a view of an emission area A of laser light at a target portion T seen from directly above. The emission area A is formed in a diamond shape due to the configuration of the laser light source 8 or by the laser light passing through a not shown lens. In FIG. 3, the right side is the intake port 12 side, and the left side is the discharge port 13 side. Therefore, an air flow F is formed flowing from the right to the left. In FIG. 3, the diamond shape showing the emission area A is divided into a top and bottom part of the two triangle shapes shown by the solid line and broken line. In other words, the diamond shape is divided into a top and bottom part along the air flow F passing through the center C of the emission area A.

The flow rate distributions at the top and bottom triangle shapes are line symmetric, so in FIG. 4 to FIG. 7, the flow rate distribution of the air flow F will be explained focusing on one divided triangle shape of the emission area A. Further, in the figures, depending on the difference in shading of the greyscale, the faster the flow rate of a region, the darker the shading shown, while the slower the flow rate of a region, the lighter the shading shown. Therefore, a black region shows a fastest flow rate, while a white region shows the slowest flow rate. Further, it is preferable to cool the entire surface of the emission area A as much as possible, so the darker the shading at the broader area in the part shown by the triangle shape, the better.

Note that, in FIG. 4 to FIG. 7, the direction of the air flow F when air supplied by the air supply device 14 is ejected from the intake port 12 to the inside of the body part 5 is made the ejection direction F0. Specifically, the ejection direction F0 is made the direction when the fastest flow rate air flow at the intake port 12 is ejected to the inside of the body part 5.

Figure 4:
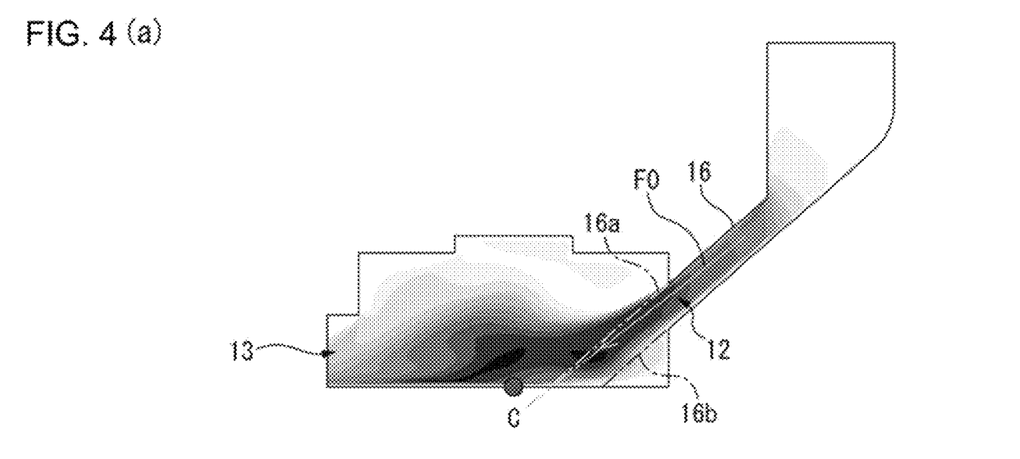
FIG. 4 is a view showing a flow rate distribution of the air flow according to an example of the present invention.

FIG. 4 is a view showing a flow rate distribution of the air flow F according to an example of the present invention. FIG. 4(a) is a vertical cross-sectional view of the front end pan of the probe 3, while FIG. 4(b) is a view showing the region of half of the emission area A of the laser light. In FIG. 4(b), the right side is the intake port 12 side, while the left side is the discharge port 13 side.

As shown in FIG. 4(a), the intake port 12 is configured so that the ejection direction F0 of the air is toward the near side of the center C of the emission area A of the laser light at the target portion T, that is, near the intake port 12. The discharge port 13 is provided at the side surface of the body part 5 near the front end part. The intake port 12 is provided at the side surface of the body part 5 further away from the front end part than the discharge port 13.

Referring to FIG. 4(a), the vicinity of the center C of the emission area A of the surface of the target portion T is shown darker. Referring to FIG. 4(b), the region is shown broader and darker from near the discharge port 13 to the center C of the emission area A and in a direction perpendicular to the ejection direction F0. In particular, as shown in FIG. 4(a), not only the direction along the ejection direction F0, but also the direction from the ejection direction F0 upward so as to go beyond the center C is shown darker, so the air flow F evenly reaches the inside of the body part 5 at the front end part as a whole. Therefore, according to the embodiment shown in FIG. 4, it is possible to efficiently cool the emission area A of the laser light, i.e., the target portion T.

Note that, instead of the ejection direction F0 of air, the air flow F may be prescribed by the shape of the intake port 12 or the duct 16. That is, the first extension line 16a at the top part of the duct 16 near the intake port 12 and the second extension line 16b at the bottom part of the duct 16 near the intake port 12 are prescribed at the vertical cross-section passing through the center of the intake port 12 and the center C of the emission area of the laser light such as shown in FIG. 4(a). At this time, as shown in FIG. 4(a), it is configured so that both the first extension line 16a and the second extension line 16b pass in front of the center C of the emission area A of the laser light at the target portion. Due to this, it is possible to prescribe a configuration with the first extension line 16a and the second extension line 16b instead of the ejection direction F0 of the air where it is possible to efficiently cool the emission area A of the laser light, i.e., the target portion T.

Figure 5A:
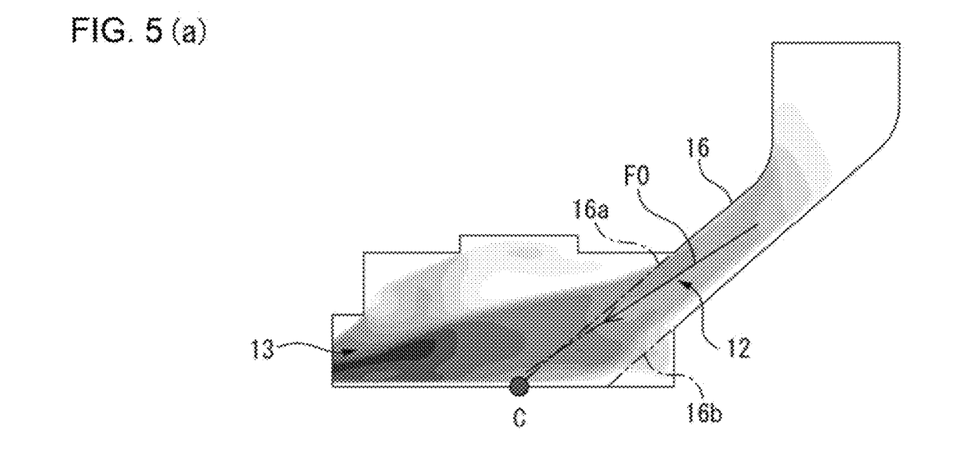
FIG. 5 is a view showing a flow rate distribution of the air flow according to a comparative example.
Figure 5B:
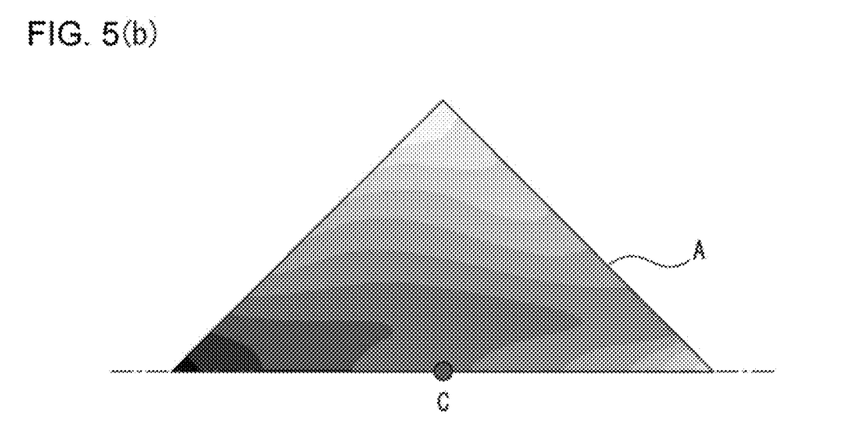

FIG. 5 is a view showing a flow rate distribution of the air flow F according to a comparative example. FIG. 5(a) is a vertical cross-sectional view of the front end part of the probe 3, while FIG. 5(b) is a view showing a region of half of the emission area A of the laser light. In FIG. 5(b), the right side is the intake port 12 side, and the left side is the discharge port 13 side.

As shown in FIG. 5(a), the intake port 12 is configured so that the ejection direction F0 of the air directly is toward the center C of the emission area A of the laser light at the target portion T. The discharge port 13 is provided at the side surface of the body part 5 near the front end part. The intake port 12 is provided at the side surface of the body part 5 further away from the front end part than the discharge port 13. Further, it is configured so that the first extension line 16a passes through the center C of the emission area A of the laser light at the target portion and the second extension line 16b runs in front of the center C of the emission area A of the laser light. Therefore, it is not configured so that both of the first extension line 16a and the second extension line 16b pass in front of the center C of the emission area A of the laser light at the target portion.

Referring to FIG. 5(a) and FIG. 5(b), compared with the example shown in FIG. 4, there is less of a region shown relatively darkly, and the shading thereof is also light. In particular, the vicinity of the discharge port 13 is shown comparatively darkly, so if the ejection direction F0 is toward the center C of the emission area A, the air flow F ends up directly heading toward the discharge port 13 and the emission area A cannot be sufficiently cooled.

Figure 6A:
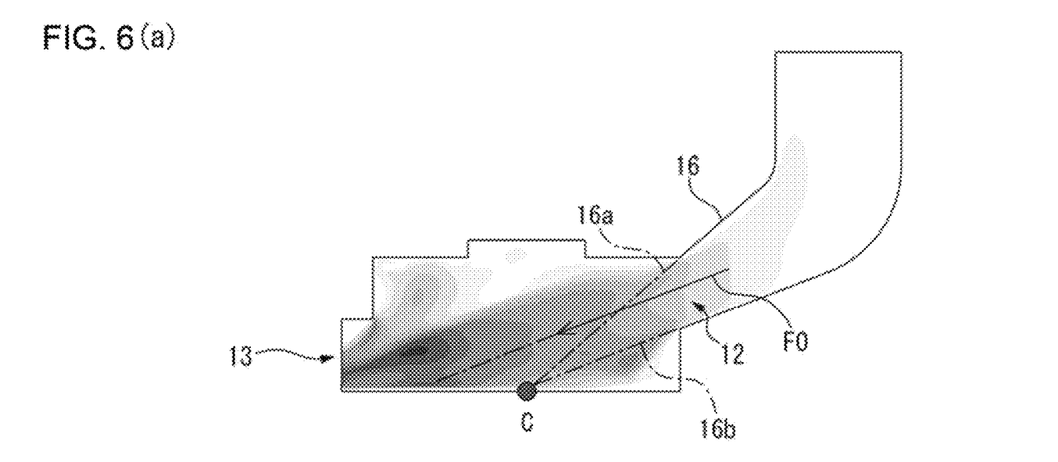
FIG. 6 is a view showing a flow rate distribution of the air flow according to another comparative example.
Figure 6B:
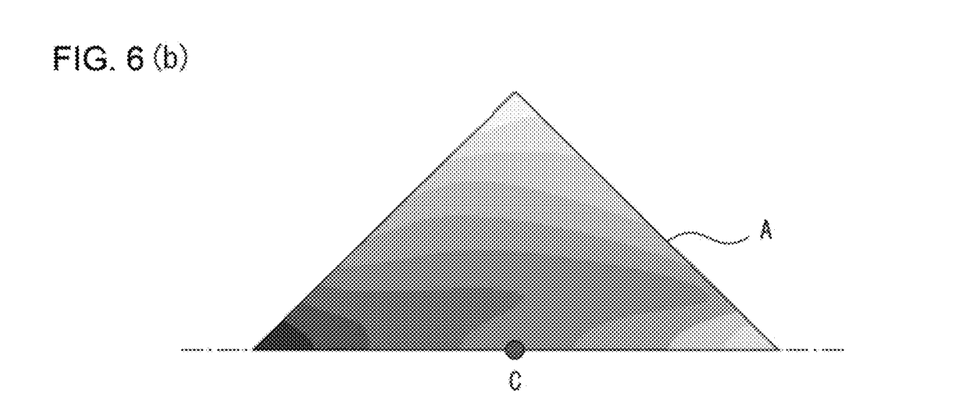

FIG. 6 is a view showing a flow rate distribution of the air flow F according to another comparative example. FIG. 6(a) is a vertical cross-sectional view of the front end part of the probe 3, while FIG. 6(b) is a view showing a region of half of the emission area A of the laser light. In FIG. 6(b), the right side is the intake port 12 side, and the left side is the discharge port 13 side.

As shown in FIG. 6(a), the intake port 12 is configured so that the ejection direction F of the air is toward the far side from the center C of the emission area A of the laser light at the target portion T. i.e., near the discharge port 13. The discharge port 13 is provided at the side surface of the body part 5 near the front end part. The intake port 12 is provided at the side surface of the body part 5 further away from the front end part than the discharge port 13. Further, it is configured so that both of the first extension line 16a and the second extension line 16b run through the center C of the emission area A of the laser light at the target portion. Therefore, it is not configured so that both of the first extension line 16a and the second extension line 16b run in front of the center C of the emission area A of the laser light at the target portion.

Referring to FIG. 6(a) and FIG. 6(b), compared with the example shown in FIG. 4, there is less of a region shown darkly and the shading thereof is also lighter. In particular, the vicinity of the discharge port 13 is shown comparatively darkly, so if the ejection direction F0 is toward the far side from the center C of the emission area A, the air flow F ends up directly heading toward the discharge port 13 and the emission area A cannot be sufficiently cooled.

Figure 7A:
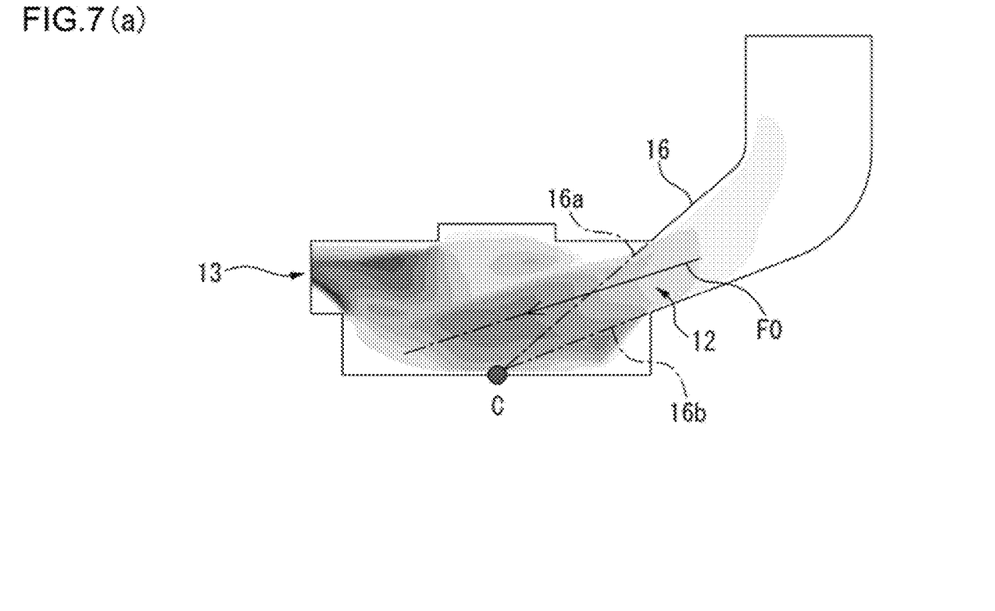
FIG. 7 is a view showing a flow rate distribution of the air flow according to still another comparative example.
Figure 7B:
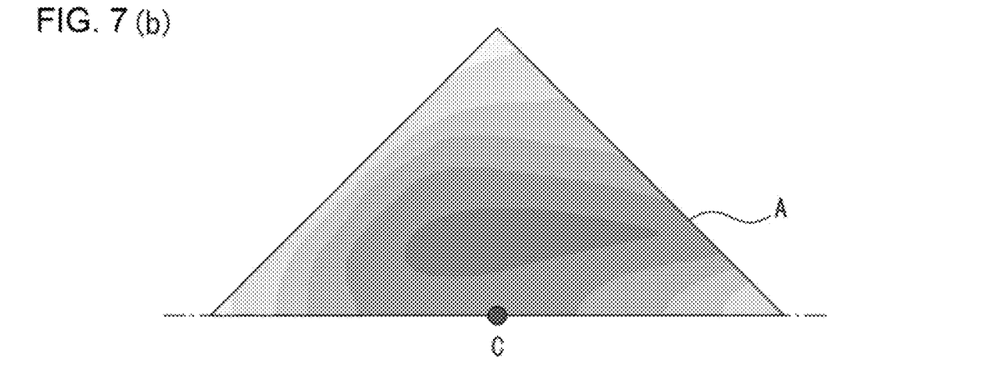

FIG. 7 is a view showing a flow rate distribution of the air flow F according to still another comparative example. FIG. 7(a) is a vertical cross-sectional view of a front end part of the probe 3, while FIG. 7(b) is a view showing a region of half of the emission area A of the laser light. In FIG. 7(b), the right side is the intake port 12 side, and the left side is the discharge port 13 side.

As shown in FIG. 7(a), the intake port 12 is configured so that the ejection direction F0 of the air is toward the far side from the center C of the emission area A of the laser light at the target portion T. The discharge port 13 is provided at the side surface of the body part 5 away from the front end pan. The intake port 12 is provided at the side surface of the body part 5 away from the front end part to the same extent as the discharge port 13. Further, both the first extension line 16a and the second extension line 16b are configured to pass through the center C of the emission area A of the laser light at the target portion. Therefore, it is not configured so that both of the first extension line 16a and the second extension line 16b run in front of the center C of the emission area A of the laser light at the target portion.

Referring to FIG. 7(a) and FIG. 7(b), there is almost no region shown darker compared with the example shown in FIG. 4. If the ejection direction F0 runs through the far side from the center C of the emission area A and the discharge port 13 is provided at the side surface of the body part 5 away from the front end part, the air flow F ends up directly heading toward the discharge port 13 and the emission area A cannot be sufficiently cooled.

As explained above with reference to FIG. 4, by configuring the intake port 12 so that the ejection direction F0 of the air is toward the near side from the center C of the emission A of the laser light in the target portion T, it is possible to efficiently cool the target portion T. In other words, when configuring the intake port 12 so that the ejection direction F0 of the air is toward the near side from the center C of the emission area A of the laser light, the angle of the ejection direction F0 with respect to the vertical direction, i.e., the angle of the intake port 12 or the duct 16 near the intake port 12, is determined in accordance with the size and shape of the intake port 12 or the flow rate of the air ejected from the intake port 12, etc. so as to enable the target portion T to be more efficiently cooled.

In the above-mentioned embodiment, the air supply device 14 supplied air by the fan 15 arranged adjoining the side surface of the body part 5 of the probe 3, but it may also supply air by a compressor, etc. provided separate from the probe 3.

REFERENCE SIGNS LIST 1. phototherapy device
2. control device
3. probe
4. cable
5. body part
6. moving part
7. optical sensor
8. laser light source
9. optical window
10. limit switch
11 opening
12 intake port
13 discharge port
14 air supply device
15 fan
16 duct
T. target portion
A. emission area

The invention claimed is:

1. A phototherapy device comprising:
   a laser light source for emitting laser light toward a target portion,
   a body part,
   an intake port provided at a side surface of the body part,
   a discharge port provided at the side surface of the body part at an opposite side from the intake port, and
   an air supply device for supplying air to be ejected from the intake port to the inside of the body part,
   the intake port is configured so that the air is ejected, at the target portion, in a direction that is toward a near side from a center of an emission area of the laser light.

2. The phototherapy device according to claim 1, wherein the discharge port is provided at the side surface of the body part near a front end part, and the intake port is provided at a position further away from the front end part of the body part than the discharge port.

3. The phototherapy device according to claim 1, wherein the air supply device has a duct connected to the intake port and, when defining a first extension line at a top part of the duct near the intake port and a second extension line at a bottom part of the duct near the intake port in a vertical cross-section passing through the center of the intake port and the center of the emission area of the laser light, the first extension line and the second extension line run in front of the center of the emission area of the laser light at the target portion.

4. The phototherapy device according to claim 3, wherein the air supply device has a fan arranged adjoining the side surface of the body part and is configured so that the duct connects the fan and the intake port and the fan generates an air flow in a direction away from the side surface of the body part.

5. The phototherapy device according to claim 1, further comprising an optical sensor having a light emitting part for emitting light toward the target portion and a light receiving part for receiving light reflected from the target portion and detecting an approach of the laser light source to the target portion up to a predetermined distance, the light emitting part and the light receiving part of the optical sensor being arranged inside the body part so as to be exposed to air ejected from the intake port.

6. The phototherapy device according to claim 5, wherein the optical sensor is arranged away from a flow path directly from the intake port to the discharge port.

* * * * *